United States Patent
Jaseer et al.

(10) Patent No.: US 11,623,901 B1
(45) Date of Patent: Apr. 11, 2023

(54) CATALYST SYSTEMS THAT INCLUDE SILYL ETHER MOIETIES

(71) Applicants: Saudi Arabian Oil Company, Dharhan (SA); King Fahd University of Petroleum and Minerals, Dhahran (SA)

(72) Inventors: EA Jaseer, Dhahran (SA); Samir Barman, Dhahran (SA); Nestor Garcia Villalta, Dhahran (SA); Motaz Khawaji, Thuwal (SA); Wei Xu, Thuwal (SA); Fahad Almalki, Thuwal (SA)

(73) Assignees: Saudi Arabian Oil Company, Dhahran (SA); King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 17/900,344

(22) Filed: Aug. 31, 2022

(51) Int. Cl.
C07C 2/34 (2006.01)
B01J 31/18 (2006.01)
B01J 31/14 (2006.01)

(52) U.S. Cl.
CPC .............. *C07C 2/34* (2013.01); *B01J 31/143* (2013.01); *B01J 31/1845* (2013.01); *C07C 2531/14* (2013.01); *C07C 2531/18* (2013.01)

(58) Field of Classification Search
None
See application file for complete search history.

(56) References Cited

U.S. PATENT DOCUMENTS

| | | |
|---|---|---|
| 2,738,151 A | 3/1956 | Herzog |
| 3,061,602 A | 10/1962 | Edward et al. |
| 3,686,350 A | 8/1972 | Ono et al. |
| 4,242,531 A | 12/1980 | Carter |
| 4,484,016 A | 11/1984 | Maschmeyer et al. |
| 4,528,415 A | 7/1985 | Knudsen |
| 4,532,370 A | 7/1985 | Le Quan et al. |
| 4,538,018 A | 8/1985 | Carter |
| 4,606,854 A | 8/1986 | Ozawa et al. |
| 4,615,998 A | 10/1986 | Le Quan et al. |
| 5,292,837 A | 3/1994 | Heinrich et al. |
| 5,376,706 A | 12/1994 | Barsotti et al. |
| 5,494,171 A | 2/1996 | Kazamoto et al. |
| 5,728,912 A | 3/1998 | Saqualain Haider Rizvi et al. |
| 5,792,895 A | 8/1998 | Commereuc et al. |
| 5,811,618 A | 9/1998 | Wu |
| 5,856,612 A | 1/1999 | Araki et al. |
| 5,877,376 A | 3/1999 | Commereuc et al. |
| 6,184,428 B1 | 2/2001 | Zahoor et al. |
| 6,767,975 B1 | 7/2004 | Liu |
| 6,903,042 B2 | 6/2005 | Drochon et al. |
| 7,122,497 B1 | 10/2006 | Nagy et al. |
| 7,157,532 B2 | 1/2007 | Payer et al. |
| 7,297,832 B2 | 11/2007 | Green et al. |
| 7,300,904 B2 | 11/2007 | Dixon et al. |
| 7,329,635 B2 | 2/2008 | Dickakian et al. |
| 7,361,623 B2 | 4/2008 | Dixon et al. |
| 7,638,597 B2 | 12/2009 | Etherton et al. |
| 7,919,569 B2 | 4/2011 | Xu et al. |
| 7,964,763 B2 | 6/2011 | Dixon et al. |
| 8,227,653 B2 | 7/2012 | Weber et al. |
| 8,252,871 B2 | 8/2012 | Miler et al. |
| 10,280,125 B2 | 5/2019 | Sogo et al. |
| 10,471,416 B2 | 11/2019 | Im et al. |
| 10,745,426 B2 | 8/2020 | Im et al. |
| 10,947,256 B2 | 3/2021 | Im et al. |
| 11,104,621 B2 | 8/2021 | Khawaji et al. |
| 2003/0109766 A1 | 6/2003 | Commereuc et al. |

(Continued)

FOREIGN PATENT DOCUMENTS

| | | |
|---|---|---|
| CN | 101189270 A | 5/2008 |
| CN | 102807632 A | 12/2012 |

(Continued)

OTHER PUBLICATIONS

Aljaralla et al. "Dimerization of Ethylene to Butene-1" Catalysis Today, 14 (1992) 1-124, 121 pgs.
Bariashier et al. "Recent advances in homogeneous chromium catalyst design for ethylene tri-, tetra-, oligo- and polymerization" Coordination Chemistry Reviews 385 (2019) 208-229, 22 pgs.
Bartlett et al. "Triptycene (9,10-o-Benzenoanthracene)" Contribution from the Converse Memorial Laboratory of Harvard University, Nov. 1942, 5 pgs.
Blann et al. "Ethylene tetramerisation: Subtle effects exhibited by N-substituted diphosphinoamine ligands" Journal of Catalysis 249 (2007) 244-249, 6 pgs.
Bollmann et al. "Ethylene Tetramerization: A New Route to Produce 1-Octene in Exceptionally High Selectivities" J. Am. Chem. Soc. 2004, 126, 2 pgs.
Elowe et al. "Nitrogen-Linked Diphosphine Ligands with Ethers Attached to Nitrogen for Chromium Catalyzed Ethylene Tri- and Tetramerizations" Arnold and Mabel Beckman Laboratories of Chemical Synthesis, 8 pgs.

(Continued)

Primary Examiner — Ali Z Fadhel
(74) Attorney, Agent, or Firm — Dinsmore & Shohl LLP

(57) ABSTRACT

Catalyst systems for tetramerizing ethylene to form 1-octene may include a catalyst which may include a chromium compound coordinated with a ligand and a co-catalyst which may include an organoaluminum compound. The ligand may have a chemical structure according to Chemical Structure (I), wherein $R_5$, $R_6$, and $R_7$ are each independently chosen from a ($C_1$-$C_{50}$) hydrocarbyl group or a ($C_1$-$C_{50}$) heterohydrocarbyl group, and wherein the ($C_1$-$C_{50}$) hydrocarbyl or ($C_1$-$C_{50}$) heterohydrocarbyl groups of $R_5$, $R_6$, and $R_7$ have greater than 10 carbon atoms combined and $R_A$, $R_B$, $R_C$, and $R_D$ and $R_1$, $R_2$, $R_3$, and $R_4$, are independently chosen from a hydrogen atom or a ($C_1$-$C_{50}$) hydrocarbyl group.

15 Claims, No Drawings

(56) References Cited

U.S. PATENT DOCUMENTS

| | | |
|---|---|---|
| 2004/0259720 A1 | 12/2004 | Sato et al. |
| 2005/0288470 A1 | 12/2005 | Benham et al. |
| 2007/0027276 A1 | 2/2007 | Cann et al. |
| 2009/0105488 A1 | 4/2009 | Cheng et al. |
| 2010/0113257 A1 | 5/2010 | Kreischer et al. |
| 2010/0190939 A1 | 7/2010 | Al-Hazmi et al. |
| 2010/0274065 A1 | 10/2010 | Sydora |
| 2012/0029258 A1 | 2/2012 | Al-Masned et al. |
| 2012/0172645 A1 | 7/2012 | Sydora |
| 2013/0123443 A1 | 5/2013 | Siraux et al. |
| 2013/0303817 A1 | 11/2013 | Shaik et al. |
| 2014/0088331 A1 | 3/2014 | Rolland |
| 2014/0250835 A1 | 9/2014 | Prabhu et al. |
| 2015/0087873 A1 | 3/2015 | Dverett et al. |
| 2015/0141605 A1 | 5/2015 | Bradin |
| 2016/0122371 A1 | 5/2016 | Lee et al. |
| 2016/0311950 A1 | 10/2016 | Batinas-Geurts et al. |
| 2016/0367977 A1 | 12/2016 | Shaikh et al. |
| 2017/0197892 A1 | 7/2017 | Khawaji et al. |
| 2017/0274356 A1 | 9/2017 | Cann et al. |
| 2019/0077816 A1* | 3/2019 | Im ............................ C07F 9/70 |
| 2019/0308179 A1 | 10/2019 | Lee et al. |
| 2020/0325165 A1 | 10/2020 | Im et al. |

FOREIGN PATENT DOCUMENTS

| | | |
|---|---|---|
| CN | 103665201 A | 3/2014 |
| CN | 103724149 A | 4/2014 |
| CN | 107778388 A | 3/2018 |
| EP | 135441 A1 | 3/1985 |
| EP | 181954 A1 | 5/1986 |
| EP | 221206 A1 | 5/1987 |
| EP | 352856 A1 | 1/1990 |
| EP | 2738151 A1 | 6/2014 |
| EP | 3231808 A1 | 10/2017 |
| EP | 3345913 A1 | 7/2018 |
| EP | 3536696 A1 | 9/2019 |
| EP | 3640232 A1 | 4/2020 |
| EP | 3805240 A1 | 4/2021 |
| JP | 02088529 A | 3/1990 |
| RU | 2561921 C1 | 9/2015 |
| WO | 2004056479 A1 | 7/2004 |
| WO | 2007088329 A1 | 8/2007 |
| WO | 2010092554 A1 | 8/2010 |
| WO | 2012013805 A1 | 2/2012 |
| WO | 2013154446 A1 | 10/2013 |
| WO | 2013168106 A1 | 11/2013 |
| WO | 2015087303 A2 | 6/2015 |
| WO | 2015087304 A2 | 6/2015 |
| WO | 2015087305 A2 | 6/2015 |
| WO | 2015118462 A1 | 8/2015 |
| WO | 2017120310 A1 | 7/2017 |
| WO | 2018106764 A1 | 6/2018 |
| WO | 2019235799 A1 | 12/2019 |

OTHER PUBLICATIONS

Farrell "Developments in Linear Alpha Olefin (LAO) Comonomer Technologies for Polyethylene" Chemsystems PERP 2011S11, May 2012, 7 pgs.

Fei et al. "Influence of the functional group on the synthesis of aminophosphines, diphosphinoamines and minobiphosphines" Dalton Trans., 2003, 2772-2779, 8 pgs.

Forestiere et al. "Oligomerization of Monoolefines by Homgeneous Catalysts" Oil & Gas Science and Technology—Rev. IFP, vol. 64 (2009) No. 6, 19 pgs.

Hennico "Butene-1 is made from ethylene" Hydrocarbon Processing, Journal vol. 69:3, 1990, Abstract Only, 2 pgs.

Karin et al. "Removal of Trace Elemental Impurities from Polyethylene by Nitric Acid" Analytical Chemistry, vol. 47, No. 13, Nov. 1975, 4 pgs.

Killian et al. "The use of bis(diphenylphosphino)amines with N-aryl functionalities in selective ethylene tri- and tetramerisation" Journal of Molecular Catalysis A: Chemical 270 (2007) 214-218, 5 pgs.

Kim et al. "Ligand Modification for Selectivity Control in Selective Ethylene Oligomerization" Macromol. Res., 26(4), 341-345(2018), 5 pgs.

Kim et al. "MAO-free and extremely active catalytic system for ethylene tetramerization" Appl Organometal Chem. 2019;33:e4829, 13 pgs.

Mole "Organoaluminium Compounds" Aust. J. Chem., 1966, 19, 381-6, 6 pgs.

Obrey et al. "A Lewis Base Promoted Alkyl/Alkoxide Ligand Redistribution: Reaction of [Me2Al(u-OCPh3)]2 with THF" Organometallics 2001, 20, 5119-5124, 6 pgs.

Pietrzykowski et al. "Reactions of methyl- and ethylaluminium compounds with alkoxyalcohols. The influence of alkoxyalchohol substituents on the structure of the complexes formed" Inorganica Chimica Acta 334 (2002) 385-394, 10 pgs.

Smith et al. "Ethylene Dimerization over Supported Titanium Alkoxides" Journal of Catalysis 105, 187-198 (1987), 12 pgs.

Sydora "Selective Ethylene Oligomerization" Organometallics 2019, 38, 997-1010, 14 pgs.

Weidman et al. "Triptycene-based copolyimides with tailored backbone rigidity for enhanced gas transport" Polymer 126(2017) 314-232, 10 pgs.

Tao, Jiang et al., "A series of novel bisphosphinoamine ligands: Synthesis, characterization and application in ethylene tetramerization", Chinese Science Bulletin, Science China Press (SCP) and Springer, CN, vol. 55, No. 33, Nov. 1, 2010, pp. 3750-3754.

Database CA [Online] Chemical Abstracts Service, Columbus, Ohio, US; 2014, Sun, Yueming et al. "Boron- and silicon-bridged bis(diphenylphosphino)-type ligands for chromium-catalyzed ethylene oligomerization", XP002805681, retrieved from STN Database accession No. 2014:525027 abstract & Sun, Yueming et al.: "Boron- and silicon-bridged bis(diphenylphosphino)-type ligands for chromium-catalyzed ethylene oligomerization" Chinese Science Bulletin, 59(21), 2613-2617; ISSN: 1001-6538, 2014.

Baojun, Zhang et al., "Cr(III)-Based Catalyst System for Oligomerization of Ethylene to 1-Octene with High Selectivity", Chinese Journal of Catalysis, vol. 28, No. 4, Jan. 1, 2007, pp. 317-320.

Chen, Hongxia et al., "Effects of halide in homogeneous Cr(III)/PNP/MAO catalytic systems for ethylene etramerization toward 1-octene", Journal of Molecular Catalysis A: Chemical, Elsevier, Amsterdam, NL, vol. 270, No. 1-2, May 7, 2007, pp. 273-277.

Kim, Eun Ho et al. "Methylaluminoxane-Free Chromium Catalytic System for Ethylene Tetramerization", ACS OMEGA, vol. 2, No. 3, Mar. 31, 2017, pp. 765-773.

Wang, Tao et al. "Mixed aluminoxanes: efficient cocatalysts for bisphosphineamine/Cr(III) catalyzed ethylene etramerization toward 1-octene", Applied Petrochemical Research, vol. 5, No. 2, Mar. 1, 2015, pp. 143-149.

\* cited by examiner

CATALYST SYSTEMS THAT INCLUDE SILYL ETHER MOIETIES

TECHNICAL FIELD

Embodiments of the present disclosure generally relate to chemical processing and, more particularly, catalyst systems utilized in such chemical processing.

BACKGROUND

Linear alpha-olefins ("LAOs") are typically produced via the cracking of refinery products or the non-selective oligomerization of ethylene, which results in a broad alpha-olefin distribution. Currently, there are several industrial processes that produce LAOS, such as the Shell Higher Olefin Process (SHOP), which has been in operation since 1977. SHOP employs a combination of oligomerization and olefin metathesis chemistries to produce a variety of LAOs using a nickel-based catalyst. INEOS, a global manufacturer of petrochemicals, has also developed a proprietary process for synthesizing a wide range of LAOs with the flexibility to change distributions of products to meet demand.

However, demand for LAOs is rising in North America, Western Europe, and Asia. In particular, demand for short chain alpha olefins, such as 1-octene and 1-hexene, is rising due to their significance to a number of specific applications. For example, 1-octene may be used to improve the rheological melt and solid resin properties of polyethylene. As a result, the main consumer of 1-octene is the industry responsible for the high-volume production of linear low-density polyethylene (LLDPE) and high-density polyethylene (HDPE), which expands each year. The content of 1-octene may be from 1% to 2% in HDPE, and as much as 30% in some LLDPE grades.

Based on this, 1-octene is a significant chemical feedstock that is in market demand. Aside from the processes discussed above, various catalysts have been developed for the tetramerization of ethylene to selectively form 1-octene. However, these catalysts have deficiencies such as fouling polymers and poor selectivity of 1-octene. Accordingly, improved catalysts, which are suitable for tetramerization of ethylene to selectively form 1-octene, are desired in the industry.

SUMMARY

Catalyst systems that include a chromium compound coordinated with a ligand may be useful for the tetramerization of ethylene to 1-octene. It has been discovered that the utilization of particular ligands in such catalyst systems may provide for enhanced anti-fouling effects. As is described herein, such ligands include an N-aryl diphosphinoamine that is substituted with a silyl ether moiety at the meta position, where the silyl ether moiety includes greater than 10 carbon atoms. Such catalyst system may improve catalytic activity, improve the selectivity of 1-octene, and reduce fouling, as compared with similar catalyst systems that do not include this particular class of ligand. Fouling, as described in the present disclosure, refers to the undesirable formation of polymers. Such polymers may form as side-products in the reaction of ethylene to form 1-octene when a catalyst system including chromium is used. Conventional ligands may also form ligand-catalyst complexes that are less soluble than those formed with the ligands of the present disclosure.

According to one or more embodiments, a catalyst system useful for tetramerizing ethylene to 1-octene is provided. The catalyst system may include a catalyst comprising a chromium compound coordinated with a ligand and a co-catalyst comprising an organoaluminum compound. The ligand may have the Chemical Structure (I):

Chemical Structure (I)

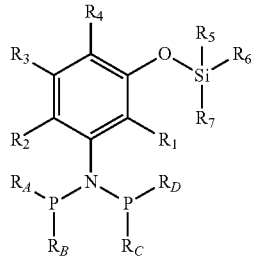

In Chemical Structure (I), P is a phosphorus atom, O is an oxygen atom, N is a nitrogen atom, and Si is a silicon atom. $R_A$, $R_B$, $R_C$, $R_D$, $R_1$, $R_2$, $R_3$, and $R_4$, may be independently chosen from a hydrogen atom, a $(C_1-C_{50})$ hydrocarbyl group, or a $(C_1-C_{50})$ heterohydrocarbyl group. $R_5$, $R_6$, and $R_7$ may each be independently chosen from a $(C_1-C_{50})$ hydrocarbyl group or a $(C_1-C_{50})$ heterohydrocarbyl group and $R_5$, $R_6$, and $R_7$ may have a combined number of carbon atoms greater than 10.

Additional features and advantages of the aspects of the present disclosure will be set forth in the detailed description that follows and, in part, will be readily apparent to a person of ordinary skill in the art from the detailed description or recognized by practicing the aspects of the present disclosure.

DETAILED DESCRIPTION

The present disclosure describes catalyst systems that may be utilized to produce 1-octene from ethylene via tetramerization. Also described are methods for utilizing such catalyst systems. The presently described catalyst systems may include a catalyst and a co-catalyst, which are described in detail herein. In one or more embodiments, the catalyst may include a chromium compound and a ligand. The co-catalyst may include an organoaluminum compound. Described herein are particular ligand structures may provide for enhanced chemical production.

In one or more embodiments, the catalyst systems described in the present disclosure may be used to selectively tetramerize ethylene to produce 1-octene, while reducing undesirable polymerization, sometimes referred to as "fouling." Fouling may occur at least partially due to the formation of solid polyethylene-based residues, which may reduce fluid flow and/or fully block or at least partially block fluids in a reactor system from flowing at a desired rate. Without being bound by any particular theory, it is believed that the incorporation of the ligand described in the present disclosure into the catalyst system may reduce fouling while maintaining a suitable yield of 1-octene.

It should be understood that the catalyst systems described in the present disclosure may not completely eliminate fouling during a reaction. However, in one or more embodiments, these catalyst systems reduce fouling as compared with catalyst systems that do not include a ligand as described in the present disclosure. Additionally, it should be understood that while these catalyst systems may be useful for the catalysis of the oligomerization of ethylene, such as the tetramerization of ethylene to form 1-octene, they may also be useful for the catalysis of other chemical reactions. As a result, these catalyst systems should not be considered limited in their use to the tetramerization of ethylene to form 1-octene.

As used in the present disclosure, the term "catalyst" refers to any substance that increases the rate of a specific chemical reaction. Catalysts described in this disclosure may be utilized to promote various reactions, such as, but not limited to, the tetramerization of ethylene to form 1-octene. Catalysts are generally not consumed in a reaction, but as would be understood in the art, may have reduced catalytic activity over time and need to be replaced and/or regenerated.

As used in the present disclosure, the term "co-catalyst" (also referred to as an activator and/or scavenger) generally refers to any substance or chemical agent that brings about catalysis of a chemical reaction in conjunction with one or more catalysts. In some embodiments, a catalyst may have independent catalytic functionality, while in other embodiments the catalyst may only have substantial catalytic functionality when paired with a co-catalyst. It should be understood that the catalyst and co-catalyst may be, in some embodiments, bonded or formed in a complex, but in other embodiments are not bonded or present in a complex. Some co-catalysts may be said to "activate" a catalyst, which may increase catalytic functionality.

As used in the present disclosure, the term "catalyst system" refers to any catalytically functional collection of chemical species. In one or more embodiments, a catalyst system may include a catalyst and a co-catalyst. In some embodiments, a catalyst system may include additional components, such as, for example, additional co-catalysts or non-catalytic additives, which may serve other purposes.

As used in the present disclosure, the term "independently chosen" means that the R groups, such as, $R_1$, $R_2$, and $R_3$, can be identical or different. For example, $R_1$, $R_2$, and $R_3$ may all be substituted alkyls; or $R_1$ and $R_2$ may be a substituted alkyl, and $R_3$ may be an aryl. A chemical name associated with an R group is intended to convey the Chemical Structure that is recognized in the art as corresponding to that of the chemical name. As a result, chemical names are intended to supplement and illustrate, not preclude, the structural definitions known to those of skill in the art.

As used in the present disclosure, the term "reaction product" refers to a chemical species formed from the reaction of any two or more reactant species or reagents. A reaction product may result in a covalent or ionic bond, coordination, or other interaction between reactant species. In one or more embodiments, two or more reaction products may result from the reaction of the reactant species, and all of these possible produced chemical species are included in the reaction product.

When used to describe certain carbon atom-containing chemical groups, a parenthetical expression having the form "$(C_x-C_y)$" means that the unsubstituted form of the chemical group has from x carbon atoms to y carbon atoms, inclusive of x and y. For example, a $(C_1-C_{50})$ alkyl group is an alkyl group having from 1 to 50 carbon atoms in its unsubstituted form. In some embodiments and general structures, certain chemical groups may be substituted by one or more substituents. A substituted chemical group defined using the "$(C_x-C_y)$" parenthetical may contain more than y carbon atoms depending on the identity of any substituents. For example, a "$(C_1-C_{50})$ alkyl substituted with exactly one phenyl ($—C_6H_5$)" may contain from 7 to 56 carbon atoms. Thus, in general when a chemical group defined using the "$(C_x-C_y)$" parenthetical is substituted by one or more carbon atom-containing substituents, the minimum and maximum total number of carbon atoms of the chemical group is determined by adding to both x and y the combined sum of the number of carbon atoms from all of the carbon atom-containing substituents.

The term "substitution" means that at least one hydrogen atom ($—H$) bonded to a carbon atom or heteroatom of a corresponding unsubstituted compound or functional group is replaced by a substituent. Substituents may be any suitable functional group or radical that could replace a hydrogen atom bonded to a carbon atom or heteroatom of a corresponding unsubstituted compound. For example, substituents may include, but are not limited to, hydrocarbyls, cyclohydrocarbyls, aryls, halogens, and amines.

The term "$—H$" means a hydrogen or hydrogen radical that is covalently bonded to another atom. "Hydrogen" and "$—H$" are interchangeable, and unless clearly specified have identical meanings.

The term "hydrocarbyl" means a monovalent radical resulting from removal of any hydrogen atom from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "heterohydrocarbyl" refers to a hydrocarbyl, from which at least one carbon atom has been replaced with a heteroatom. Examples of heteroatoms include, without limitation, oxygen, nitrogen, sulfur, and phosphorus.

The term "cyclohydrocarbyl" means an aromatic or non-aromatic, cyclic hydrocarbyl having at least three carbon atoms, including monocyclic and polycyclic hydrocarbyls, fused and non-fused polycyclic hydrocarbyls, and bicyclic hydrocarbyls, non-aromatic saturated or unsaturated cyclic hydrocarbyls, and substituted or unsubstituted hydrocarbyls.

The term "aryl" means an aromatic hydrocarbon radical, in which the carbon atoms of the aromatic system may be substituted or unsubstituted. Aryls include monocyclic, bicyclic and tricyclic aromatic hydrocarbon radicals. A monocyclic aromatic hydrocarbon radical includes one aromatic ring; a bicyclic aromatic hydrocarbon radical has two rings; and a tricyclic aromatic hydrocarbon radical has three rings. When the bicyclic or tricyclic aromatic hydrocarbon radical is present, at least one of the rings of the radical is aromatic. The other ring or rings of the aromatic radical may be independently fused or non-fused and aromatic or non-aromatic. Non-limiting examples of aryls include phenyl; fluorenyl; tetrahydrofluorenyl; indacenyl; hexahydroindacenyl; indenyl; dihydroindenyl; naphthyl; tetrahydronaphthyl; and phenanthrenyl.

The term "alkyl" means a saturated hydrocarbon radical that may be linear or branched. Accordingly, the term "$(C_1-C_{20})$ alkyl" means a saturated linear or branched hydrocarbon radical of from 1 to 20 carbon atoms that is unsubstituted or substituted. Examples of unsubstituted $(C_1-C_{20})$ alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1-C_{20})$ alkyl include trifluoromethyl and trifluoroethyl.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents, one or more double and/or triple bonds optionally may be present in substituents. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents, if any, or in aromatic rings or heteroaromatic rings, if any.

As noted previously, the embodiments of the present disclosure are directed to a catalyst system suitable for tetramerizing ethylene to form 1-octene. In one or more embodiments, the catalyst system includes a catalyst. In some embodiments, the catalyst includes chromium. It should be understood that, as contemplated in the present disclosure, a catalyst that includes chromium may be any chemical compound that includes chromium and is catalytically functional for, without limitation, promoting the tetramerization of ethylene to form 1-octene.

In one or more embodiments, the catalyst includes a chromium compound and a ligand. It should be understood that the chromium compounds described herein, which may coordinate with one or more ligands, are not necessarily limited in structure, but include any compound that includes chromium and that can coordinate with one or more of the ligands described herein. In some embodiments, the chromium compound includes an organic chromium salt, an inorganic chromium salt, a chromium coordination complex, a chromium organometallic complex, or combinations of these. In some embodiments, the chromium compound includes a chromium trichloride tris-tetrahydrofuran complex, chromium dichloride bis-tetrahydrofuran complex, (benzene)tricarbonyl chromium, chromium (III) octanoate, chromium (III) acetylacetonate, chromium hexacarbonyl, chromium (III) 2-ethylhexanoate, chromium (III) 2,2,6,6-tetramethyl-3,5-heptanedionate, or combinations of these.

The chromium compound may be produced using procedures and methods known in the art. For example, procedures and methods for producing the chromium compound are described in U.S. Pat. No. 7,297,832, which is incorporated by reference in its entirety.

It should be understood that the ligands described herein, which may coordinate with chromium in the chromium compound are not necessarily limited in structure. However, in one or more embodiments, the ligand may have a structure according to Chemical Structure (I):

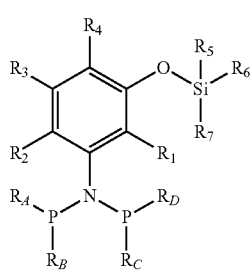

Chemical Structure (I)

In Chemical Structure (I), P is a phosphorus atom, O is an oxygen atom, N is a nitrogen atom, and Si is a silicon atom. $R_A$, $R_B$, $R_C$, $R_D$, $R_1$, $R_2$, $R_3$, and $R_4$, may be independently chosen from a hydrogen atom, a $(C_1-C_{50})$ hydrocarbyl group, or a $(C_1-C_{50})$ heterohydrocarbyl group. $R_5$, $R_6$, and $R_7$ may each be independently chosen from a $(C_1-C_{50})$ hydrocarbyl group or a $(C_1-C_{50})$ heterohydrocarbyl group and $R_5$, $R_6$, and $R_7$ may have a combined number of carbon atoms greater than 10. As used in the present disclosure, the term "combined number of carbon atoms" refers to the total number of carbon atoms of the groups chosen for $R_5$, $R_6$, and $R_7$. For example, if $R_5$, $R_6$, and $R_7$ are all unsubstituted $(C_4)$ hydrocarbyl groups then the combined number of carbon atoms of $R_5$, $R_6$, and $R_7$ would be 12 $(C_4+C_4+C_4)$.

As described herein, the presently disclosed ligands include an N-Aryl diphosphinoamine that is substituted with a silyl ether group. A generalized N-Aryl diphosphinoamine structure is shown in Chemical Structure (II).

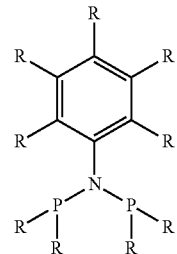

Chemical Structure (II)

Without being bound by theory, it is believed that N-Aryl diphosphinoamine ligands, as shown in Chemical Structure (II) may undergo isomerization to form an iminobiphosphine ligand as shown in Chemical Structure (III). It is further believed that the iminobiphosphine isomer may be inactive to the tetramerization of ethylene to form 1-octene. It is also believed that the iminobiphosphine isomer may facilitate, during the tetramerization of ethylene, the formation of polyethylene residues, which may contribute to unwanted fouling. Without being bound by theory, it is believed that N-aryl diphosphinoamine ligands with an electron withdrawing group substitution may undergo isomerization to the iminobiphosphine isomer. It is also believed that N-aryl diphosphinoamine ligands with electron releasing group substitutions at the meta-position, like the ligands presently described may stabilize the diphosphinoamine structure and reduce isomerization to the iminobiphosphine isomer. In Chemical Structure (I), for example, an N-aryl diphosphinoamine ligand is substituted with a silyl ether moiety at the meta position of the ligand. It is believed that a silyl ether moiety substituted at the meta positon may function as an electron releasing group which may reduce isomerization to the undesired iminobiphosphine isomer.

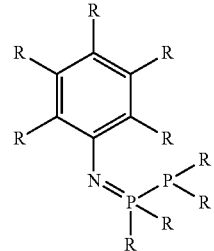

Chemical Structure (III)

Referring again to Chemical Structure (I), as described herein, in one or more embodiments, $R_A$, $R_B$, $R_C$, $R_D$, $R_1$, $R_2$, $R_3$, and $R_4$ may be a ($C_1$-$C_{50}$) hydrocarbyl group. In embodiments, the ($C_1$-$C_{50}$) hydrocarbyl group may be a substituted or unsubstituted ($C_1$-$C_{50}$) linear or branched hydrocarbyl group, a substituted or unsubstituted ($C_3$-$C_{50}$) cyclohydrocarbyl group, or a substituted or unsubstituted ($C_4$-$C_{50}$) aryl group. In some embodiments, $R_A$, $R_B$, $R_C$, $R_D$, $R_1$, $R_2$, $R_3$, and $R_4$ may be independently chosen from a hydrogen atom, a substituted or unsubstituted ($C_1$-$C_{50}$) linear or branched alkyl group, a substituted or unsubstituted ($C_3$-$C_{50}$) cyclohydrocarbyl group, or a substituted or unsubstituted ($C_6$-$C_{50}$) aryl group. In some embodiments, one or more of $R_A$, $R_B$, $R_C$, and $R_D$ may comprise aryl moieties. In some embodiments, $R_A$, $R_B$, $R_C$, and $R_D$ may be independently chosen from a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl, or tetrahydrofuranyl group. In an exemplary embodiment, $R_1$, $R_2$, $R_3$, and $R_4$ may be a hydrogen atom and $R_A$, $R_B$, $R_C$, and $R_D$ may be a phenyl group.

In one or more embodiments, one or more of $R_A$, and $R_B$ or $R_C$ and $R_D$, may be bonded with P in Chemical Structure (I) such that a cyclic moiety is formed. For example, $R_A$ and $R_B$ may be bonded such that a cyclic moiety including P is formed. Likewise, $R_C$ and $R_D$ may be bonded such that a cyclic moiety including P is formed. In one or more embodiments, $R_A$, $R_B$, and P may form a phospholane group. In one or more embodiments, $R_C$, $R_D$, and P may form a phospholane group. As described herein, a "phospholane group" refers to a cyclic organophosphorous compound comprising a five membered ring including phosphorous and four carbon atoms. In some embodiments, the phospholane compound may be unsubstituted or may be substituted by one or more hydrocarbyl groups. Cyclic moieties that may be formed from $R_A$, $R_B$, and P or $R_C$, $R_D$, and P in some embodiments are depicted in Chemical Structures (IV) to (XI).

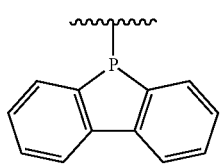

Chemical Structure (IV)

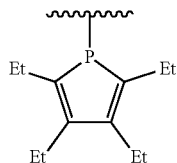

Chemical Structure (V)

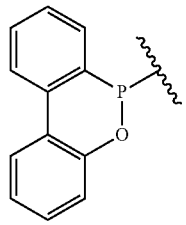

Chemical Structure (VI)

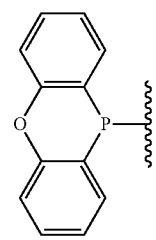

Chemical Structure (VII)

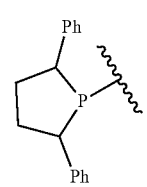

Chemical Structure (VIII)

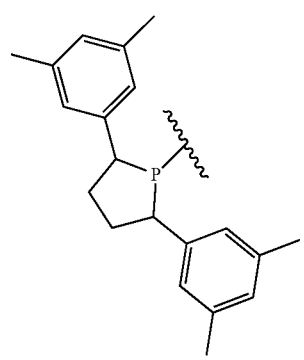

Chemical Structure (IX)

Chemical Structure (X)

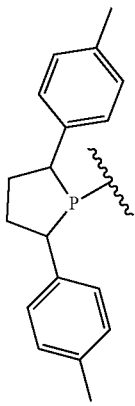

Chemical Structure (XI)

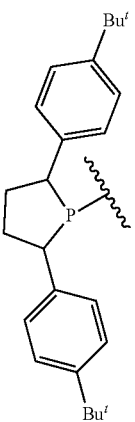

Referring back to Chemical Structure (I), as described herein, in one or more embodiments, $R_5$, $R_6$, and $R_7$ may each be independently chosen from a ($C_1$-$C_{50}$) hydrocarbyl group or a ($C_1$-$C_{50}$) heterohydrocarbyl group. In embodiments, the ($C_1$-$C_{50}$) hydrocarbyl group may be a substituted or unsubstituted ($C_1$-$C_{50}$) linear or branched hydrocarbyl group, a substituted or unsubstituted ($C_3$-$C_{50}$) cyclohydrocarbyl group, or a substituted or unsubstituted ($C_4$-$C_{50}$) aryl group. In embodiments, the ($C_1$-$C_{50}$) heterohydrocarbyl group may be a substituted or unsubstituted ($C_1$-$C_{50}$) linear or branched heterohydrocarbyl group or a substituted or unsubstituted ($C_3$-$C_{50}$) cycloheterohydrocarbyl group.

As described herein, in one or more embodiments, $R_5$, $R_6$, and $R_7$ may have a combined number of carbon atoms greater than 10. For example, $R_5$, $R_6$, and $R_7$ may have a combined number of carbon atoms greater than 15, greater than 20, greater than 30, greater than 40, greater than 50, greater than 60, greater than 70, greater than 80, greater than 90, greater than 100, greater than 110, greater than 120, greater than 130, greater than 140, or even greater than 150. Without being bound by theory, it is believed that the ligand-catalyst complex may have improved solubility, when the combined number of carbon atoms of $R_5$, $R_6$, and $R_7$ is greater than 10, when compared to a ligand-catalyst complex where $R_5$, $R_6$, and $R_7$ have a combined number of carbon atoms less than or equal to 10. This improved solubility may improve the ligand-catalyst complex's catalytic activity, selectivity for 1-octene, and may reduce fouling when compared to a less soluble ligand-catalyst complex.

In some embodiments, $R_5$, $R_6$, and $R_7$ may each independently be an unsubstituted linear or branched ($C_1$-$C_{50}$) alkyl group. For example, $R_5$, $R_6$, and $R_7$ may be independently chosen from a methyl, ethyl, 1-propyl, 2-propyl, 1-butyl, 2-butyl, 2-methylpropyl, 1,1-dimethylethyl, 1-pentyl, 1-hexyl, 1-heptyl, 1-nonyl, or 1-decyl group. In some embodiments, $R_5$, $R_6$, and $R_7$ may each independently be an unsubstituted ($C_4$-$C_{20}$) linear alkyl group.

In one or more embodiments, one or more of $R_5$, $R_6$, and $R_7$ may independently be a substituted or unsubstituted aryl group and $R_5$, $R_6$, and $R_7$ may have a combined number of carbon atoms greater than 10. In some embodiments, one or more of $R_5$, $R_6$, and $R_7$ may independently be a substituted or unsubstituted aryl group and $R_5$, $R_6$, and $R_7$ may have a combined number of carbon atoms greater than 15. For example, $R_5$, $R_6$, and $R_7$ may each independently be chosen from a phenyl, fluorenyl, tetrahydrofluorenyl, indacenyl, hexahydroindacenyl, indenyl, dihydroindenyl, naphthyl, tetrahydronaphthyl, or phenanthrenyl group.

In one or more embodiments, one or more of $R_5$, $R_6$, and $R_7$ may be a ($C_1$-$C_{50}$) heterohydrocarbyl group and $R_5$, $R_6$, and $R_7$ may have a combined number of carbon atoms greater than 10.

In some embodiments, $R_1$, $R_2$, $R_3$, and $R_4$ may be a hydrogen atom. $R_A$, $R_B$, $R_C$, and $R_D$ may be a phenyl group, and $R_5$, R6, and R7 are each independently an unsubstituted ($C_4$-$C_{20}$) linear alkyl group. In an exemplary embodiment, $R_1$, $R_2$, $R_3$, and $R_4$ may be a hydrogen atom. $R_A$, $R_B$, $R_C$, and $R_D$ may be a phenyl group, and $R_5$, R6, and R7 are each 1-butyl.

In one or more embodiments, the catalyst may include the ligand in an amount such that a molar ratio of the ligand to chromium in the catalyst is from 0.1 to 10.0. For example, the molar ratio of the ligand to chromium in the catalyst may be from 0.1 to 9.0, from 0.1 to 8.0, from 0.1 to 7.0, from 0.1 to 6.0, from 0.1 to 5.0, from 0.1 to 4.0, from 0.1 to 3.0, from 0.1 to 2.0, from 0.1 to 1.0, from 0.1 to 0.5, from 0.5 to 10.0, from 0.5 to 9.0, from 0.5 to 8.0, from 0.5 to 7.0, from 0.5 to 6.0, from 0.5 to 5.0, from 0.5 to 4.0, from 0.5 to 3.0, from 0.5 to 2.0, from 0.5 to 1.0, from 1.0 to 10.0, from 1.0 to 9.0, from 1.0 to 8.0, from 1.0 to 7.0, from 1.0 to 6.0, from 1.0 to 5.0, from 1.0 to 4.0, from 1.0 to 3.0, from 1.0 to 2.0, from 2.0 to 10.0, from 2.0 to 9.0, from 2.0 to 8.0, from 2.0 to 7.0, from 2.0 to 6.0, from 2.0 to 5.0, from 2.0 to 4.0, from 2.0 to 3.0, from 3.0 to 10.0, from 3.0 to 9.0, from 3.0 to 8.0, from 3.0 to 7.0, from 3.0 to 6.0, from 3.0 to 5.0, from 3.0 to 4.0, from 4.0 to 10.0, from 4.0 to 9.0, from 4.0 to 8.0, from 4.0 to 7.0, from 4.0 to 6.0, from 4.0 to 5.0, from 5.0 to 10.0, from 5.0 to 9.0, from 5.0 to 8.0, from 5.0 to 7.0, from 5.0 to 6.0, from 6.0 to 10.0, from 6.0 to 9.0, from 6.0 to 8.0, from 6.0 to 7.0, from 7.0 to 10.0, from 7.0 to 9.0, from 7.0 to 8.0, from 8.0 to 10.0, from 8.0 to 9.0, from 9.0 to 10.0, or from any combination of these ranges.

In one or more embodiments, the catalyst system also includes a co-catalyst. In some embodiments, the co-catalyst may include an organoaluminum compound. As described in the present disclosure, the term "organoaluminum compound" refers to any chemical compound that includes at least one aluminum atom and any organic moiety. It should be appreciated that the organoaluminum compound may include several chemical species, or may be a single chemical species. In some embodiments, the organoaluminum compound may be an alkyl aluminum compound. The alkyl aluminum compound may, for example, have a structure according to Chemical Structure (XII):

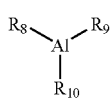

Chemical Structure (XII)

In Chemical Structure (XII), $R_8$, $R_9$, and $R_{10}$ are each independently chosen from a hydrogen atom, a ($C_1$-$C_{20}$) hydrocarbyl group, or a ($C_1$-$C_{20}$) heterohydrocarbyl group. In embodiments, the ($C_1$-$C_{20}$) hydrocarbyl group may be a substituted or unsubstituted ($C_1$-$C_{20}$) linear or branched hydrocarbyl group. In one or more embodiments, $R_8$, $R_9$, and $R_{10}$ may each be a hydrogen atom or a linear or branched ($C_1$-$C_{20}$) alkyl group. In some embodiments, the alkyl aluminum compound may be an aluminoxane structure (a partial hydrolysate of a trialkylaluminum compound). For example, suitable aluminum alkyl compounds may include trimethylaluminium, triethylaluminum, tripropylaluminum, tri-iso-butylaluminum, diisobutylaluminium hydride, tri-hexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), and modified alkylaluminoxanes, such as modified methylaluminoxane (MMAO). As described in the present disclosure, the term "modified alkylaluminoxane" refers to an alkylaluminoxane that includes one or more modifier groups, such as isobuytyl or n-octyl groups in addition to the alkyl groups. In one or more embodiments, the organoaluminum compound of the catalyst system may comprise, consist essentially of, or consist of any of these compounds.

Without intending to be bound by theory, the alkyl aluminum compound may be operable to remove impurities, or poisons that may have a negative effect on the catalyst. Additionally, the alkyl aluminum compound may be operable to alkylate the chromium compound. Furthermore, the alkyl aluminum compound may be operable to activate the chromium compound to allow the coordination of the ethylene with the catalyst.

In one or more embodiments, the catalyst system may include the co-catalyst in an amount such that a molar ratio of the organoaluminum compound to the chromium compound in the catalyst system is from 100 to 5000. For example the molar ratio of the organoaluminum compound to the chromium compound in the catalyst system may be from 100 to 4500, from 100 to 4000, from 100 to 3500, from 100 to 3000, from 100 to 2500, from 100 to 2000, from 100 to 1500, from 100 to 1000, from 100 to 500, from 500 to 5000, from 500 to 4500, from 500 to 4000, from 500 to 3500, from 500 to 3000, from 500 to 2500, from 500 to 2000, from 500 to 1500, from 500 to 1000, from 1000 to 5000, from 1000 to 4500, from 1000 to 4000, from 1000 to 3500, from 1000 to 3000, from 1000 to 2500, from 1000 to 2000, from 1000 to 1500, from 1500 to 5000, from 1500 to 4500, from 1500 to 4000, from 1500 to 3500, from 1500 to 3000, from 1500 to 2500, from 1500 to 2000, from 2000 to 5000, from 2000 to 4500, from 2000 to 4000, from 2000 to 3500, from 2000 to 3000, from 2000 to 2500, from 2500 to 5000, from 2500 to 4500, from 2500 to 4000, from 2500 to 3500, from 2500 to 3000, from 3000 to 5000, from 3000 to 4500, from 3000 to 4000, from 3000 to 3500, from 3500 to 5000, from 3500 to 4500, from 3500 to 4000, from 4000 to 5000, from 4000 to 4500, from 4500 to 5000, or from any combination of these ranges.

In one or more embodiments, ethylene may be contacted with the catalyst system to from a reaction product including 1-octene. Contacting may generally include any mixing and/or combining of the reactant ethylene with the catalyst system. In some embodiments, the catalyst and co-catalyst may be separately prepared as solutions, and then combined, prior to contacting of the catalyst system with ethylene. In some embodiments, the catalyst system may be contacted with ethylene in the presence of one or more reaction mediums. Suitable reaction mediums may include, for example, cyclohexane (CyH), methylcyclohexane (MeCy), decahydronapthalene (DHN), chlorobenzene (PhCl), toluene, xylene, heptane, and isooctane, but other suitable reaction mediums are contemplated herein. In some embodiments, the ethylene may be contacted with the catalyst system in the presence of hydrogen.

In one or more embodiments, the reaction may be performed as a batch reaction or as a continuous process reaction, such as a continuous stir tank reactor process. In some embodiments, the pressure of the reactor may be from 2 bar to 100 bar (such as from 10 bar to 60 bar), and the reactor temperature may be from 30° C. to 120° C. (such as from 30° C. to 100° C.). However, process conditions outside of these ranges are contemplated, especially in view of the specific design of the reactor system and concentrations of the reactants and catalyst system.

It should be understood that, in one or more embodiments, similar catalyst systems that do not include the ligand of the present application may exhibit increased fouling compared to the catalyst system of the present application. In one or more embodiments, the inclusion of the ligand in a catalyst system may suppress polymer formation while not greatly reducing the yield of 1-octene. In one or more embodiments, polymer formation (fouling) may be reduced by at least 5% or hither by the use of the ligand. For example, the reaction product of the tetramerization of ethylene using the catalyst system may include less than 99 wt. % to less than 10 wt. % of polymer.

In one or more embodiments, 1-octene production may be increased, stay the same, or may decrease by less than or equal to 100% to 5% by the inclusion of the ligand. For example, the reaction product of the tetramerization of ethylene using the catalyst system may include from greater than 5 wt. % to 100 wt. % of 1-octene.

In one or more embodiments, the catalyst system may both reduce the polymer formation from 5% to 99.9% and increase, not effect, or decrease 1-octene production rate by less than or equal to 100% to 5%. Reduction in polymer formation rates and catalytic activity on a percentage basis are based on catalyst systems that include the ligand of the present disclosure as compared with catalyst systems that do not include the ligand of the present disclosure.

In one or more embodiments, the catalyst system may have increased activity compared to similar catalyst systems that do not include the ligand of the present disclosure. As used in the present disclosure, the term "activity" refers to the amount of reaction product produced (in kilograms) per the amount of chromium metal used (in grams) per hour ($kg \cdot g_{Cr}^{-1} \cdot h^{-1}$). In some embodiments, the catalyst system may have an activity greater than 10 $kg \cdot g_{Cr}^{-1} \cdot h^{-1}$, or greater than 100 $kg \cdot g_{Cr}^{-1} \cdot h^{-1}$ to 5000 $kg \cdot g_{Cr}^{-1} \cdot h^{-1}$. For example, the catalyst system may have an activity from, from 100 $kg \cdot g_{Cr}^{-1} \cdot h^{-1}$ to 4000 $kg \cdot g_{Cr}^{-1} \cdot h^{-1}$, from 100 $kg \cdot g_{Cr}^{-1} \cdot h^{-1}$ to 3000 $kg \cdot g_{Cr}^{-1} \cdot h^{-1}$, from 100 $kg \cdot g_{Cr}^{-1} \cdot h^{-1}$ to 2000 $kg \cdot g_{Cr}^{-1} \cdot h^{-1}$, from 100 $kg \cdot g_{Cr}^{-1} \cdot h^{-1}$ to 1000 $kg \cdot g_{Cr}^{-1} \cdot h^{-1}$, from 100 $kg \cdot g_{Cr}^{-1} \cdot h^{-1}$ to 500 $kg \cdot g_{Cr}^{-1} \cdot h^{-1}$, from 500 $kg \cdot g_{Cr}^{-1} \cdot h^{-1}$ to 5000 $kg \cdot g_{Cr}^{-1} \cdot h^{-1}$, from 500 $kg \cdot g_{Cr}^{-1} \cdot h^{-1}$ to 4000 kg·$g_{Cr}^{-1}$·$h^{-1}$, from 500 kg·$g_{Cr}^{-1}$·$h^{-1}$ to 3000 kg·$g_{Cr}^{-1}$·$h^{-1}$, from 500 kg·$g_{Cr}^{-1}$·$h^{-1}$ to 2000 kg·$g_{Cr}^{-1}$·$h^{-1}$, from 500 kg·$g_{Cr}^{-1}$·$h^{-1}$ to 1000 kg·$g_{Cr}^{-1}$·$h^{-1}$, from 1000 kg·$g_{Cr}^{-1}$·$h^{-1}$ to 5000 kg·$g_{Cr}^{-1}$·$h^{-1}$, from 1000 kg·$g_{Cr}^{-1}$·$h^{-1}$ to 4000 kg·$g_{Cr}^{-1}$·$h^{-1}$, from 1000 kg·$g_{Cr}^{-1}$·$h^{-1}$ to 3000 kg·$g_{Cr}^{-1}$·$h^{-1}$, from 1000 kg·$g_{Cr}^{-1}$·$h^{-1}$ to 2000 kg·$g_{Cr}^{-1}$·$h^{-1}$, from 2000 kg·$g_{Cr}^{-1}$·$h^{-1}$ to 5000 kg·$g_{Cr}^{-1}$·$h^{-1}$, from 2000 kg·$g_{Cr}^{-1}$·$h^{-1}$ to 4000 kg·$g_{Cr}^{-1}$·$h^{-1}$, from 2000 kg·$g_{Cr}^{-1}$·$h^{-1}$ to 3000 kg·$g_{Cr}^{-1}$·$h^{-1}$, from 3000 kg·$g_{Cr}^{-1}$·$h^{-1}$ to 5000 kg·$g_{Cr}^{-1}$·$h^{-1}$, from 3000 kg·$g_{Cr}^{-1}$·$h^{-1}$ to 4000 kg·$g_{Cr}^{-1}$·$h^{-1}$, or from 4000 kg·$g_{Cr}^{-1}$·$h^{-1}$ to 5000 kg·$g_{Cr}^{-1}$·$h^{-1}$.

EXAMPLES

The various aspects of the present disclosure will be further clarified by the following examples. The examples are illustrative in nature and should not be understood to limit the subject matter of the present disclosure.

Example 1—Preparation m-tris-n-Butyl silyloxy-N-Aryl-PNP ligand

A ligand was formed as depicted in Reaction Scheme 1:

Reaction Scheme (1)

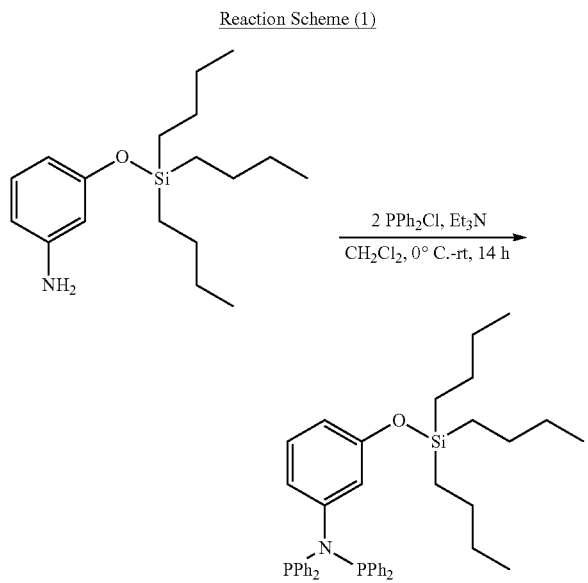

First, $C_6H_4$(m-tris-n-Bu-silyloxy)$NH_2$ (0.507 g, 1.65 mmol), triethylamine (0.50 g, 4.95 mmol), and 5 mL of dichloromethane was combined to make a solution. To the solution, chlorodiphenylphosphine (0.72 g, 3.3 mmol) was slowly added at 0° C. The mixture was stirred for one hour and allowed to warm up to room temperature followed by additional stirring for 14 hours. The volatiles were removed under reduced pressure and the residue was extracted with anhydrous tetrahydrofuran (3×3 mL). After removing the tetrahydrofuran, the remaining oily compound was triturated with anhydrous acetonitrile (5×2 mL) followed by degassing at 50° C. to yield the desired ligand as a white solid. The yield was 65%.

Example 2—Ethylene Tetramerization Utilizing the Ligand of Example 1

Multiple ethylene tetramerization runs were performed in a magnetically stirred (1000 rotations per minute (rpm)) stainless steel reactor system (250 ml; commercially available from Buchi), which was equipped with a propeller-like stirrer and injection barrel for charging solvents and reagents. The reactor system was first heated to 110° C., purged several times with argon and ethylene to remove air and moisture, and then cooled to the desired temperature. A solution of the co-catalyst, containing 2 mmol of modified methylaluminoxane (MMAO), was then prepared via dilution with chlorobenzene to a total volume of 95 ml. Next, a catalyst solution was prepared by dissolving 1 μmol of chromium (III) acetylacetonate (Cr(acac)$_3$) in 1 mL of chlorobenzene. The ligand synthesized in Example 1 was separately dissolved in 1 mL of chlorobenzene before being combined with the (Cr(acac)$_3$) solution and diluted to a total volume of 5 ml. The co-catalyst and catalyst solutions had a total solution volume of 100 mL. The ratio of ligand to chromium was 1:1. The solutions were then transferred to the reactor system, which was then pressurized to 45 bar (4.5 MPa) using ethylene to initiate ethylene tetramerization. The temperature of the reactor system was maintained constant during ethylene tetramerization by circulating relatively warm oil through a jacket of the reactor system and relatively cool liquid through a cooling coil of the reactor system as necessary.

After 10 minutes, methanol (1.0 ml) was added to quench ethylene tetramerization. The reactor system was then cooled to approximately 15° C. and then was slowly depressurized using a needle valve. Next, an aliquot of the liquid inside the reaction system was collected and quantified via gas chromatography (GC) analysis. The liquid remaining in the reaction system was collected, added to 50 ml of acidic methanol (5% HCl), and stirred at room temperature for 2 hours. Polymer was then filtered from the mixture, washed with distilled water, and stirred in water (200 ml) for 1 hour. This process was repeated four times. Finally, the polymer was filtered and dried in a vacuum oven at 60° C. overnight. The results of the tetramerization reaction at different reaction temperatures were reported in Table 1.

As reported in Table 1, productivity refers to the amount of reaction product produced (in kilograms) per the amount of chromium metal used (in grams) per hour (kg·$g_{Cr}^{-1}$·$h^{-1}$). The references to $C_6$, $C_8$, and $C_{10+}$ refer to the amount of hydrocarbons, in weight percent of the total reaction product, with 6 total carbon atoms, 8 total carbon atoms, or with greater than 10 total carbon atoms respectively. 1-$C_6$ and 1-$C_8$ refer to the weight percentage of the $C_6$ and $C_8$ products that were 1-hexene and 1-octene respectively. PE refers to the amount of polyethylene that was formed in weight percent of the total reaction product. The production of polyethylene may be associated with fouling.

TABLE 1

| Temperature (° C.) | Productivity (kg · $g_{Cr}^{-1}$ · $hr^{-1}$) | $C_6$ (wt. %) | 1-$C_6$ (in $C_6$) (wt. %) | $C_8$ (wt. %) | 1-$C_8$ (in $C_8$) (wt. %) | 1-$C_6$ + 1-$C_8$ (wt. %) | $C_{10+}$ (wt. %) | PE (wt. %) |
|---|---|---|---|---|---|---|---|---|
| 60 | 2036 | 25.6 | 74.1 | 63.9 | 97.3 | 81.1 | 0.9 | 9.6 |
| 75 | 894 | 32.6 | 84.6 | 54.0 | 95.7 | 79.2 | 0.1 | 13.3 |

As Table 1 indicates, the m-silyloxy(tris-n-Bu) PNP ligand has high selectivity for the desired 1-hexene and the 1-octene isomers. The ligand also tetramerizes ethylene at a high rate (>2000 kg·$g_{Cr}^{-1}$·$h^{-1}$) and provides more than 50 wt. % $C_8$ products. Further, the ligand produces only a small amount of fouling polymer (PE) as at both tested temperatures less than 15 wt. % of the fouling polymer was produced and when the reaction was run at 60° C. less than 10 wt. % of fouling polymer was produced.

In a first aspect of the present disclosure, a catalyst system for tetramerizing ethylene to form 1-octene may comprise a catalyst which comprises a chromium compound coordinated with a ligand and a co-catalyst which comprises an organoaluminum compound. The ligand has a chemical structure according to Chemical Structure (I), wherein $R_5$, $R_6$, and $R_7$ are each independently chosen from a ($C_1$-$C_{50}$) hydrocarbyl group or a ($C_1$-$C_{50}$) heterohydrocarbyl group, and wherein the ($C_1$-$C_{50}$) hydrocarbyl or ($C_1$-$C_{50}$) heterohydrocarbyl groups of $R_5$, $R_6$, and $R_7$ have greater than 10 carbon atoms combined and $R_A$, $R_B$, $R_C$, and $R_D$ and $R_1$, $R_2$, $R_3$, and $R_4$, are independently chosen from a hydrogen atom or a ($C_1$-$C_{50}$) hydrocarbyl group.

A second aspect of the present may include the first aspect where $R_5$, $R_6$, and $R_7$ are each independently an unsubstituted ($C_1$-$C_{50}$) linear or branched alkyl group.

A third aspect of the present disclosure may include either the first or second aspects where $R_5$, $R_6$, and $R_7$ are each independently an unsubstituted ($C_4$-$C_{20}$) linear alkyl group.

A fourth aspect of the present disclosure may include any of the first through third aspects where one or more of $R_5$, $R_6$, and $R_7$ are substituted or unsubstituted aryl groups, and wherein $R_5$, $R_6$, and $R_7$ have greater than 15 carbon atoms combined.

A fifth aspect of the present disclosure may include any of the first through fourth aspects where one or more of $R_A$, $R_B$, $R_C$, and $R_D$ are substituted or unsubstituted aryl moieties.

A sixth aspect of the present disclosure may include any of the first through fifth aspects where $R_1$, $R_2$, $R_3$, and $R_4$ are each a hydrogen atom and $R_A$, $R_B$, $R_C$, and $R_D$ are each a phenyl group.

A seventh aspect of the present disclosure may include any of the first through sixth aspects where the chromium compound comprises one or more of an organic chromium salt, an inorganic chromium salt, a chromium coordination complex, and a chromium organometallic complex.

An eighth aspect of the present disclosure may include any of the first through seventh aspects where the chromium compound comprises one or more of chromium trichloride tris-tetrahydrofuran complex, chromium dichloride bis-tetrahydrofuran complex, (benzene)tricarbonyl chromium, chromium (III) octanoate, chromium (III) acetylacetonate, chromium hexacarbonyl, chromium (III) 2-ethylhexanoate, and chromium (III) 2,2,6,6-tetramethyl-3,5-heptanedionate.

A ninth aspect of the present disclosure may include any of the first through eighth aspects where the catalyst comprises the ligand in an amount such that a molar ratio of the ligand to chromium is from 0.1 to 10.0.

A tenth aspect of the present disclosure may include any of the first through ninth aspects where the organoaluminum compound has the chemical structure according to Chemical Structure (XII) where $R_8$, $R_9$, and $R_{10}$ are each selected from the group consisting of a hydrogen atom and an unsubstituted ($C_1$-$C_{20}$) linear or branched alkyl group.

An eleventh aspect of the present disclosure may include any of the first through tenth aspects where the organoaluminum compound comprises one or more of trimethylaluminum, triethylaluminum, tripropylaluminum, tri-iso-butylaluminum, diisobutylaluminium hydride, trihexylaluminum, tri-n-octylaluminum, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane, ethylaluminoxane, and modified methylaluminoxane.

A twelfth aspect of the present disclosure may include any of the first through eleventh aspects where the catalyst system comprises the co-catalyst in an amount such that a molar ratio of the organoaluminum compound to the chromium compound is from 100 to 5000.

A thirteenth aspect of the present disclosure may include a method for tetramerizing ethylene to form 1-octene, the method comprising contacting ethylene with the catalyst system of the first through twelfth aspects to form a product comprising 1-octene A fourteenth aspect of the present disclosure may include the thirteenth aspect where the 1-octene is formed in conditions of a reactor pressure of from 2 bar to 100 bar and a reactor temperature from 30° C. to 180° C.

A fifteenth aspect of the present disclosure may include the thirteenth or fourteenth aspects where ethylene is contacted with the catalyst system in the presence of a reaction medium, where the reaction medium comprises one or more of cyclohexane, methylcyclohexane, decahydronapthalene, chlorobenzene, toluene, xylene, heptane, and isooctane.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

For the purposes of describing and defining the present disclosure it is noted that the terms "about" or "approximately" are utilized in this disclosure to represent the inherent degree of uncertainty that may be attributed to any quantitative comparison, value, measurement, or other representation. The terms "about" and/or "approximately" are also utilized in this disclosure to represent the degree by which a quantitative representation may vary from a stated reference without resulting in a change in the basic function of the subject matter at issue.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

Additionally, the term "consisting essentially of" is used in this disclosure to refer to quantitative values that do not materially affect the basic and novel characteristic(s) of the disclosure. For example, a chemical composition "consisting essentially" of a particular chemical constituent or group of chemical constituents should be understood to mean that the composition includes at least about 99.5% of a that particular chemical constituent or group of chemical constituents.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition should be appreciated as containing, in some embodiments, a mixture of isomers of that constituent. In additional embodiments, the chemical compounds may be present in alternative forms such as derivatives, salts, hydroxides, etc.

What is claimed is:

1. A catalyst system for tetramerizing ethylene to form 1-octene, the catalyst system comprising:
   a catalyst comprising a chromium compound coordinated with a ligand; and
   a co-catalyst comprising an organoaluminum compound, wherein:
   the ligand has the chemical structure:

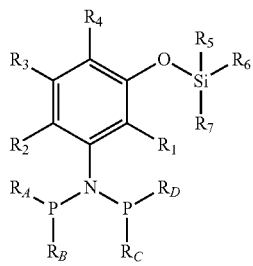

wherein:
$R_5$, $R_6$, and $R_7$ are each independently chosen from a ($C_1$-$C_{50}$) hydrocarbyl group or a ($C_1$-$C_{50}$) heterohydrocarbyl group, and wherein the ($C_1$-$C_{50}$) hydrocarbyl or ($C_1$-$C_{50}$) heterohydrocarbyl groups of $R_5$, $R_6$, and $R_7$ have greater than 10 carbon atoms combined; and
$R_A$, $R_B$, $R_C$, and $R_D$ and $R_1$, $R_2$, $R_3$, and $R_4$, are independently chosen from a hydrogen atom or a ($C_1$-$C_{50}$) hydrocarbyl group.

2. The catalyst system of claim 1, wherein $R_5$, $R_6$, and $R_7$ are each independently an unsubstituted ($C_1$-$C_{50}$) linear or branched alkyl group.

3. The catalyst system of claim 1, wherein $R_5$, $R_6$, and $R_7$ are each independently an unsubstituted ($C_4$-$C_{20}$) linear alkyl group.

4. The catalyst system of claim 1, wherein one or more of $R_5$, $R_6$, and $R_7$ are substituted or unsubstituted aryl groups, and wherein $R_5$, $R_6$, and $R_7$ have greater than 15 carbon atoms combined.

5. The catalyst system of claim 1, wherein one or more of $R_A$, $R_B$, $R_C$, and $R_D$ are substituted or unsubstituted aryl moieties.

6. The catalyst system of claim 1, wherein:
$R_1$, $R_2$, $R_3$, and $R_4$ are each a hydrogen atom; and
$R_A$, $R_B$, $R_C$, and $R_D$ are each a phenyl group.

7. The catalyst system of claim 1, wherein the chromium compound comprises one or more of an organic chromium salt, an inorganic chromium salt, a chromium coordination complex, and a chromium organometallic complex.

8. The catalyst system of claim 1, wherein the chromium compound comprises one or more of chromium trichloride tris-tetrahydrofuran complex, chromium dichloride bis-tetrahydrofuran complex, (benzene)tricarbonyl chromium, chromium (III) octanoate, chromium (III) acetylacetonate, chromium hexacarbonyl, chromium (III) 2-ethylhexanoate, and chromium (III) 2,2,6,6-tetramethyl-3,5-heptanedionate.

9. The catalyst system of claim 1, wherein the catalyst comprises the ligand in an amount such that a molar ratio of the ligand to chromium is from 0.1 to 10.0.

10. The catalyst system of claim 1, wherein the organoaluminum compound has the structure:

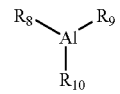

wherein $R_8$, $R_9$, and $R_{10}$ are each selected from the group consisting of a hydrogen atom and an unsubstituted ($C_1$-$C_{20}$) linear or branched alkyl group.

11. The catalyst system of claim 1, wherein the organoaluminum compound comprises one or more of trimethylaluminium, triethylaluminum, tripropylaluminum, tri-isobutylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane, ethylaluminoxane, and modified methylaluminoxane.

12. The catalyst system of claim 1, wherein the catalyst system comprises the co-catalyst in an amount such that a molar ratio of the organoaluminum compound to the chromium compound is from 100 to 5000.

13. A method for tetramerizing ethylene to form 1-octene, the method comprising contacting ethylene with the catalyst system of claim 1 to form a product comprising 1-octene.

14. The method of claim 13, wherein the 1-octene is formed in conditions of:
a reactor pressure from 2 bar to 100 bar; and
a reactor temperature from 30° C. to 180° C.

15. The method of claim 13, wherein ethylene is contacted with the catalyst system in the presence of a reaction medium, wherein the reaction medium comprises one or more of cyclohexane, methylcyclohexane, decahydronapthalene, chlorobenzene, toluene, xylene, heptane, and isooctane.

* * * * *